United States Patent [19]

Gomes de Matos et al.

[11] Patent Number: 4,740,635

[45] Date of Patent: * Apr. 26, 1988

[54] PROCESS FOR CRYSTALLIZING BISPHENOL-A

[75] Inventors: Isabel M. Gomes de Matos; Gaylord M. Kissinger, both of Evansville, Ind.

[73] Assignee: General Electric Company, Mt. Vernon, Ind.

[ * ] Notice: The portion of the term of this patent subsequent to Apr. 26, 2005 has been disclaimed.

[21] Appl. No.: 920,463

[22] Filed: Oct. 20, 1986

[51] Int. Cl.$^4$ .................... C07C 37/84; C07C 39/16

[52] U.S. Cl. .................... 568/724; 568/727; 568/748; 568/749

[58] Field of Search ............... 568/724, 723, 722, 748, 568/749, 727

[56] References Cited

U.S. PATENT DOCUMENTS

| | | |
|---|---|---|
| 4,209,646 | 6/1980 | Gac et al. ................ 568/724 |
| 4,212,997 | 7/1980 | Adams et al. ............ 568/724 |
| 4,461,915 | 7/1984 | Mendiratta .............. 568/724 |
| 4,529,823 | 7/1985 | Mendiratta .............. 568/724 |
| 4,533,764 | 8/1985 | Chang et al. ............ 568/724 |
| 4,638,102 | 1/1987 | Little ...................... 568/724 |

*Primary Examiner*—Werren B. Lone
*Attorney, Agent, or Firm*—Martin B. Barancik

[57] ABSTRACT

A process for crystallizing bisphenol-A which comprises:

a. adding water to a mixture comprising bisphenol-A, about 0.5 to 15 weight percent of diphenol isomers and impurities, said mixture essentially free of phenol, b. maintaining the combined water and said mixture of (a) at a temperature sufficient to melt the solid material of step (a), c. adiabatically cooling the water and said mixture to below about 90° C., and d. separating crystalline bisphenol-A from the mother liquor.

7 Claims, No Drawings

PROCESS FOR CRYSTALLIZING BISPHENOL-A

BACKGROUND OF THE INVENTION

The diphenol 2,2 bis-(4-hydroxyphenyl)propane, otherwise known as bisphenol-A, is a well known phenol in the commercial world. It is used in the preparation of many polymers including polyarylates, copolyester-carbonates, polycarbonates, epoxies and other polymeric materials. In order to make polycarbonates, a high quality bisphenol-A is required. Therefore, substantial attention has been directed to the methods of preparing and isolating relatively pure bisphenol-A. Researchers in the past have taken advantage of the fact that bisphenol-A and phenol, one of the two starting materials in preparing bisphenol-A, form a 1:1 molar adduct which lends itself to purification. Processes which start with the isolation and purification of bisphenol-A through the treatment of an adduct are disclosed in U.S. Pat. No. 4,209,646, Gac, et al, issued to Rhone-Poulenc Industries and U.S. Pat. No. 4,212,997, Adams, et al, issued to General Electric Company. In Gac, impure bisphenol-A, phenol and less than about 15% by weight of water is brought to a temperature wherein the mixture is entirely liquid. It is then cooled to a temperature less than about 60° C. while applying reduced pressure to the mixture to form the adduct of bisphenol-A and phenol which crystallizes. The phenol is then removed from the bisphenol-A so as to obtain the bisphenol-A apart from phenol. The temperature which is generally necessary to maintain the mixture in this liquid state prior to the adiabatic cooling step is from about 70° to 100° C. In Adams, et al an adduct between the bisphenol-A and phenol is also the starting point in the process. The temperature of the mixture is lowered from the point at which bisphenol-A is soluble to a temperature from which the adduct crystallizes. The adduct is recovered and mixed with an excess of water at a temperature to completely melt the adduct. The water present is an amount sufficient to retain the phenol portion of the adduct upon separation of bisphenol-A from the phenol, and then lowering the temperature of the water and melted adduct to cause the separation of the bisphenol-A portion of the adduct from the phenol.

Additionally, U.S. Pat. No. 3,326,986, Dugan, et al, issued to Dow Chemical Company shows the crystallization of bisphenol-A from its isomers and excess phenol through the addition of water and heating to a temperature sufficient to melt the crude bisphenol-A and other impurities, followed by cooling to affect the crystallization of the bisphenol-A. Sufficient phenol is present to form a substantial amount of adduct.

It has now been found that substantial quantities of adduct of bisphenol-A and phenol are not necessary to prepare crystalline bisphenol-A in pure form. Rather, an impure form of bisphenol-A with essentially no phenol present can be the starting point for crystallization and purification steps. This allows for the preparation of very pure bisphenol-A in high yield from the crude bisphenol-A prepared by art known methods. The process also has the advantages of being done in a continuous phase if desired.

SUMMARY OF THE INVENTION

In accordance with the invention there is a process for crystallizing and purifying bisphenol-A which comprises a. adding water to a mixture comprising bisphenol-A, about 0.5 to 15 weight percent of diphenol isomers and impurities, said mixture essentially free of phenol, b. maintaining the combined water and said mixture of (a) at a temperature sufficient to melt the solid material of step a;

c. adiabatically cooling the water and said mixture to below about 90° C., thereby causing crystalline bisphenol-A to form; and d. separating crystalline bisphenol-A from the mother liquor.

A further aspect of the invention is further purifying the crystallized bisphenol-A contaminated with isomers of bisphenol-A and other phenolic impurities by contacting the said bisphenol-A with a mixture of phenol, bisphenol-A and water in weight percentages of 0–95, 0–50, and 5–100 respectively and separating the purified bisphenol-A from the said wash mixture.

A still further aspect of the invention is the combination of the crystallization and further purification steps to obtain a further purified crystallized bisphenol-A from bisphenol-A contaminated with isomers.

A further preferred aspect of the invention is to wash the slurry of formed bisphenol-A crystals while in contact with the mother liquor prior to step d above with a mixture of phenol, bisphenol-A and water in weight percentages 0–95, 0–50, and 5–100 respectively.

DETAILED DESCRIPTION OF THE INVENTION

The typical method of preparing bisphenol-A is through the condensation reaction of phenol and acetone in the presence of an acidic catalyst system. Although the reaction is quite selective to the p,p' addition of the ketone to the phenolic system, still a certain amount of isomers are formed. These isomers sometimes known as "other phenolic impurities" are compounds such as the ortho p' isomer specifically 2,4'-isopropylidenediphenol, p-(2,2,4-trimethyl-4-chromanyl) phenol, sometimes known as "dianines" and 4,4' (4-hydroxy-m-phenylenediisopropylidene)diphenyl, sometimes known as "trisphenol". Clearly other isomers or phenolic impurities can also be present along with bisphenol-A and the previously named isomers. This mixture of bisphenol-A, isomers and excess phenol can then be heated under standard conditions to remove virtually all of the phenol.

The starting material for the process steps in accordance with this invention is a crude bisphenol-A mixture containing about 0.5 to 15 weight percent isomers, i.e. phenolic impurities, as measured by the weight of bisphenol-A present. Generally the isomers and phenolic impurities vary from about 3 to 8 weight percent. This crude bisphenol is essentially free of phenol. By essentially free is meant at least less than about 0.5 weight percent phenol as measured by the bisphenol-A present. It is preferably less than about 0.3 weight percent phenol. This is in marked contrast to the starting material of other crystallization and purification processes wherein substantial quantities of phenol is present up to and including the actual adduct of bisphenol-A and phenol which is a 1:1 molar adduct.

To this crude bisphenol-A mixture is now added a significant quantity of water. Generally the ratio of water to crude bisphenol-A is between about 1:1 and 3:1 on a weight basis as measured by the crude bisphenol-A mixture. The water added is preferably 1.5 to 2.5 on a weight basis. The mixture is brought to a temperature or maintained at a temperature, depending upon the initial temperature of the crude bisphenol-A mixture, which will melt all the solid material therein. Generally this temperature is from about 95° to 105° C. while still maintaining the liquid state of the mixture due to the presence of the additional bisphenol-A mixture which raises the boiling point of the water.

The water, crude bisphenol-A mixture is now cooled adiabatically, while stirring, by reducing the pressure. The temperature is brought down to below a temperature of about 90° C., generally within a range of from about 45° to about 89° C. wherein the bisphenol-A crystallizes from the solution. The preferred temperature to which the mixture of water and crude bisphenol-A are cooled is to a temperature of from about 55° to about 75° C. The crystallized bisphenol-A is readily separated from the mother liquor by centrifugation and/or filtration or other standard methods. A substantial separation has occurred between the bisphenol-A and the isomers and/or other phenolic impurities which are present. Depending upon the use of the bisphenol-A, such purity may be sufficient. If further purity of the bisphenol-A is required, standard washing techniques may be employed.

It is a further aspect of the invention that a new contacting step which further purifies the crystallized bisphenol-A is now applicable. The bisphenol-A crystals are contacted with a mixture of phenol, bisphenol-A and water in a weight ratio respectively of about 0 to 95, 0 to 50 and 5 to 95. Based on the quantity of bisphenol-A present, a wash weight ratio of from about 1:1 to 3:1 wash:bisphenol-A can be employed. Any residual phenol now present can be removed by a water wash. The invention wash can be repeated up to three times or more depending upon the purity which one desires. The presence of the bisphenol-A in the water wash seems to provide a better separation of the bisphenol-A from the isomers and phenolic impurities and helps maintain the bisphenol-A in crystalline form. The temperature at which the wash is performed is not unduly significant, however elevated temperatures of from about 45° to about 75° C. are preferred. The specific ratio of the wash components employed is at least somewhat dependent upon the balance of yield versus purity of the crystallized bisphenol-A desired. If more phenol is present the yield of crystallized bisphenol-A is reduced. This can be somewhat counter-balanced by the presence of bisphenol-A in the wash mixture. With phenol present, the purity is higher and also allows the wash to be performed at a lower temperature as opposed to that without phenol. If one uses no phenol, the yield of crystallized bisphenol-A is generally higher and the wash can be performed at a higher temperature, >95° C. It is generally preferred to use greater than 50 weight percent water in the wash.

The wash mixture can also be used as a prewash of crystalline bisphenol-A which is in contact with the mother liquor. Prior to separating the crystalline bisphenol-A, the slurry of bisphenol-A in mother liquor can be contacted with the identified wash mixture.

Below are examples of the invention. The crude bisphenol-A mixture starting material utilized in the examples is comprised of the following components:

| COMPONENT | WT. % |
| --- | --- |
| Bisphenol-A | 93.3 |
| o-p'bisphenol-A | 2.7 |

-continued

| COMPONENT | WT. % |
| --- | --- |
| phenol | .08 |
| others | 3.9 |

The examples are intended to illustrate the scope of the invention and are not intended to limit that scope.

EXAMPLE 1

In a flask are placed 200 gms of crude bisphenol-A and 400 gms of deionized water. While stirring the mixture was brough to a boil, about 103° C., until all the crude BPA was molten. The contents of the flask was transferred to a 1,000 ml crystallizer vessel which had been preheated to about 100° C. While stirring, vacuum was pulled until the mixture reached 85° C. The mixture was held for 10 minutes at this temperature then vacuum was pulled further until the temperature was brought to 65° C. Crystals of bisphenol-A had already formed. At this temperature a mixture of 40 gms phenol/60 gms bisphenol-A/23 gms of water at a previously held temperature of 65° C. was added to the slurry and stirred. The mixture was held for one minute. The mixture was added to a 2000 ml filter funnel and the crystalline bisphenol-A separated.

The filter cake of crystalline bisphenol-A was washed with a mixture of 6.7 gms phenol/10 gms bisphenol-A/50 gms water previously brought to a temperature of 65° C. for nine times. The filter cake was then washed three times with 200 gms of deionized water at 65° C. The crystalline bisphenol-A was dried in a vacuum oven at 15 mm Hg for 1½ hours at 105° C.

The quality of the bisphenol-A was very good showing an initial absorbance of 0.111.

EXAMPLE 2

The experimental procedure of Example 1 was followed. The final quality of the bisphenol-A was 0.104 initial absorbance. The composition of the final bisphenol-A was measured by high pressure liquid chromatography which gave the analysis below:

| COMPONENT | WT. % |
| --- | --- |
| Bisphenol-A | 99.22 |
| o-p'bisphenol-A | 0.4 |
| phenol | 0.16 |
| others | 0.2 |

EXAMPLE 3

The experimental procedure of Example 1 was followed except that the slurry washing was done with a mixture of 40 gms phenol/40 gms bisphenol-A/20 gms water and the wash of the separated crystallized bisphenol-A was performed three times with a wash mixture of 20 gms phenol/20 gms bisphenol-A/160 gms water. The quality of the bisphenol-A was 0.12 initial absorbance. The purity of the bisphenol-A was measured by high pressure liquid chromatography which provided the following analysis:

| COMPONENT | WT. % |
| --- | --- |
| Bisphenol-A | 99.15 |
| o-p'bisphenol-A | 0.43 |
| phenol | 0.03 |

| COMPONENT | WT. % |
| --- | --- |
| others | 0.38 |

What is claimed is:

1. A process for crystallizing bisphenol-A which comprises:
   a. adding water to a mixture comprising bisphenol-A, about 0.5 to 15 weight percent of diphenol isomers and impurities, said mixture essentially free of phenol, the water in a weight ratio of 1:1 to 3:1 based on the weight of the said mixture
   b. maintaining the combined water and said mixture of (a) at a temperature sufficient to melt the solid material of step (a),
   c. adiabatically cooling the water and said mixture to below about 90° C., and
   d. separating crystalline bisphenol-A from the mother liquor.

2. The process in accordance with claim 1 wherein about 3 to 8 weight percent of bisphenol-A isomers and impurities are present.

3. The process in accordance with claim 1 wherein the adiabatically cooling brings the water and said mixture to a temperature between about 45° and 89° C.

4. The process in accordance with claim 1 wherein prior to step d the crystalline bisphenol-A in contact with the mother liquor is contacted with a mixture comprising phenol, bisphenol-A and water in weight percentage respectively of 0 to 95, 0 to 50, and 5 to 95.

5. The process in accordance with claim 1 wherein the separated crystallized bisphenol-A is washed with a mixture comprising phenol, bisphenol-A, water in weight percentages respectively of 0 to 95, 0 to 50, and 5 to 95.

6. The process in accordance with claim 4 wherein the separated crystallized bisphenol-A is washed with a mixture comprising phenol, bisphenol-A, water in weight percentages respectively of 0 to 95, 0 to 50, and 5 to 95.

7. A process for purifying crystalline bisphenol-A contaminated with isomers of bisphenol-A and other impurities comprising contacting the said bisphenol-A with a mixture comprising phenol, bisphenol-A and water in weight percentages respectively of 0 to 95, 0 to 50, and 5 to 95 and thereafter separating the purified crystalline bisphenol-A from the mixture.

* * * * *